United States Patent [19]
Kandil et al.

[11] Patent Number: 6,080,589
[45] Date of Patent: Jun. 27, 2000

[54] *NEISSERIA MENINGITIDIS* CAPSULAR POLYSACCHRIDE CONJUGATES

[75] Inventors: Ali Kandil, Willowdale; Pele Chong, Richmond Hill; Michel H. Klein, Willowdale, all of Canada

[73] Assignee: Connaught Laboratories Limited, North York, Canada

[21] Appl. No.: 09/061,189

[22] Filed: Apr. 17, 1998

Related U.S. Application Data

[62] Division of application No. 08/474,392, Jun. 7, 1995, Pat. No. 5,780,606.

[51] Int. Cl.$^7$ ........................ G01N 33/563; A61K 38/16; C12P 21/08; C07K 1/00
[52] U.S. Cl. ........................ 436/512; 514/8; 514/54; 530/308.1; 530/395; 536/18.7; 536/53; 536/55.3; 536/12.3; 536/124
[58] Field of Search .................. 536/18.7, 53, 35.3, 536/125, 123.1; 514/54, 8; 530/388.1, 395; 436/512

[56] References Cited

U.S. PATENT DOCUMENTS

| | | | |
|---|---|---|---|
| 4,258,029 | 3/1981 | Moloney et al. | 424/88 |
| 4,727,136 | 2/1988 | Jennings et al. | |
| 4,855,283 | 8/1989 | Lockhoff et al. | 514/8 |
| 4,882,317 | 11/1989 | Marburg et al. | 514/54 |
| 5,141,743 | 8/1992 | Schryvers | 424/92 |

FOREIGN PATENT DOCUMENTS

| | | |
|---|---|---|
| 0161188 | 11/1985 | European Pat. Off. |
| WO 92/10936 | 7/1992 | WIPO |
| WO 92 16232 | 10/1992 | WIPO |
| WO 94 05325 | 3/1994 | WIPO |
| WO 94/12641 | 6/1994 | WIPO |

OTHER PUBLICATIONS

Jennings, H. J. et al, vol. 127, Sep. 1981, pp. 1011–1018.
Jennings, H. J. et al, Journal of Immunology, vol. 137, No. 5, Sep. 1, 1986, pp. 1708–1713.
Devi, S. J. N. et al, Proceedings of the National Academy of Sciences of USA, vol. 88, No. 16, Aug. 15, 1991, pp. 7175–7179.
Devi et al. *Proc. Natl. Acad. Sci. USA* Aug. 1991, 88, 7175–7179.
Fattom et al. *Infect. Immun.* Feb. 1992, 60(2), 584–589.
Jackson, L.A., and Wenger, J.D. Laboratory–based surveillance for meningococcal disease in selected areas, United States, 1989–1991, MMW R 1993, 42: 21–30.
Peltola, H.; Kayhty, H.; Makela, P.H. (1977) *Haemophilus influenzae* type b capsular polysaccharide vaccine in children: a double blind field study 100,00 vaccines 3 months to 5 years of age in Finland, *Pediatrics* 60: 730–737.
Gotschlich EC (1984) Meningococcal meningitis. In: Germanier E (ed) *Bacterial vaccines*, Academic, New York, pp. 237–255.
Ding, S.Q., Ye R.B., Zhang H.C. (1981) Three new serogroups of *Neisseria meningitidis, J. Biol. Stand* 9: 307–315.
Ashton FE, Ryan A. Diena B. Jennings HJ (1983) A new serogroup (L) of *Neisseria meningitidis, J. Clin. Microbiol.* 17: 722–727.
Gotschlich EC, Goldschneider I, Artenst2ein MS (1969a) Human immunity to the meningococcus IV. Immunogenicity of group A and group C meningococcal polysaccharides. *J. Exp Med.* 129: 1367–1384.
Artenstein MS, Gold R., Zimmerly JG, Wyle FA, Schneider H. Harkins C. (1970) Prevention of meningococcal disease by group C polysaccharides vaccine. *N Engl. J. Med.* 282: 417–420.
Cadoz M, Armand J. Arminjon F., Gire R., Laflax C. (1985) Tetravelent (Ak, C, Y, W135) meningococcal vaccine in children: immunogenicity and safety, *Vaccine* 3: 340–342.
Wyle FA, Artenstein MS, Brandt BL, Tramont EC, Kasper DL, Alteri PL, Berman SL, Lowenthal JP (1972) Immunologic response of man to group B meningococcal polysaccharide vaccines. *J. Infect Dis.* 126: 514–521.
Zollinger, W. D. Mandrell, R. E., Griffiss, J. M., Altieri, P., and Berman, S. 1979, *J. Clin. Invest.* 63, 836.
Gotschlich, E. C., Fraser, B. A., Nishimura, D., Robbins, J. B. Liu, T.–Y. 1981, *J. Biol. Chem.* 256, 8915.
Zollinger, W. D., Mandrell, R. E., Griffis, J. M. Seminars in infection Disease. New York, Thieme–Stranon, 1980, vol. 4: *Bacterial Vaccines,* p. 254.
Mandrell, R. E., Zollinger, R. E., 1982, *J. Immunol.* 129, 2172.
Jennings, H. J., Lugowsky, C 1981, *J. Immunol.* 137, 1708.
Jennings, H. J., Roy, Gamian, A. 1986, *J. Immunol.* 137, 1708.
Svennerholm, L. (1957), *Biochimica and Biophysica Acta.* 24, 604.
Jennings, H. J.(1989), Cruse, J. M, Lewis, R. E. Jr. (eds): *Conjugate Vaccines.* Basel, Karger, vol. 10, pp. 151–165.
Lockhoff, O. Glycolipids as Immunomodulators: Synthesis and Properties. (1991), *Chem. Int. Ed. Engl.* 30:1611–1620.
Nixon–George et al. (1990), *J. Immunology* 144: 4798–4802.
Jennings, HJ., Capsular Polysaccharides as Vaccine Candidates. Current Topics in Microbiology and Immunology. 1990, 150: 97–127.
Jennings, HJ., Capsular Polysaccharides as human vaccines. Advance in Carbohydrate Chemistry and Biochemistry, 1983, 41: 155.
Jennings, H. J., Roy, R, Michon, F. (1985), *J. Immunol.* 134, 2651.

*Primary Examiner*—Elli Peselev
*Attorney, Agent, or Firm*—Sim & McBurney

[57] ABSTRACT

Capsular polysaccharides containing multiple sialic acid residues, particularly the Group B polysaccharide of *Neisseria meningitidis*, are modified by chemical reaction to randomly introduce pendant reactive residues of heterobifunctional linker molecules to the polysaccharide backbone. The capsular polysaccharide is deacetylated and the heterobifunctional linker molecule is reacted with the deacetylated material and any residual amino groups are blocked by reaction with alkyl acid anhydride. The introduction of the linker molecules to the polysaccharide chain between the termini enables the polysaccharide to be linked to a carrier molecule, such as a protein, to enhance the immunogenicity of the polysaccharide. The conjugate molecule may be formulated as an immunogenic composition for raising antibodies in a host to the polysaccharide.

31 Claims, 3 Drawing Sheets

1. R = R' = H
2. R = R' = COCH₃
3. R = H, R' = COCH₃
4. R = COCH₃, R' = H

NEISSERIA MENINGITIDIS CAPSULAR POLYSACCHRIDE CONJUGATES

This application is a division of Application Ser. No. 08/474,392, filed Jun. 7, 1995, now U.S. Pat. No. 5,780,606.

FIELD OF INVENTION

The present invention is related to the field of immunology and is particularly concerned with polysaccharide/protein conjugate molecules.

BACKGROUND OF THE INVENTION

Following the introduction of polysaccharide vaccines against Meningococcus A, C, Y and W135 and the conjugate vaccine against *Haemophilus influenzae* type b, Meningococcus B (MenB) is the major cause of meningitis worldwide. In the United States alone, Group B *Neisseria meningitidis* cause 46% of total meningitis cases (ref. 1—Throughout this application, various references are referred to in parenthesis to more fully describe the state of the art to which this invention pertains. Full bibliographic information for each citation is found at the end of the specification, immediately preceding the claims. The disclosures of these references are hereby incorporated by reference into the present disclosure). Meningococcal meningitis occurs in both endemic and epidemic forms. Epidemic disease occurs in all parts of the world and incidences as high as 500 per 100,000 have been reported. Without antibiotic treatment the mortality is exceedingly high (85%) and even with this treatment it still remains at approximately 10%. In addition, patients cured by antibiotic therapy can still suffer serious and permanent neurologic deficiencies. These facts together with the emergence of sulfadiazine-resistant strains promoted the rapid development of a commercial vaccine (ref. 2).

Meningitidis is a gram-negative bacterium that has been classified serologically into groups A, B, C, 29e, W135, X, Y and Z. Additional groups H, I, and K were isolated in China (ref. 4) and group L was isolated in Canada (ref. 5). The grouping system is based on the capsular polysaccharides of the organism.

In contrast to the pneumococcal vaccine, the composition of the meningococcal polysaccharide vaccine has been greatly simplified by the fact that fewer polysaccharides are required. In fact groups A, B, and C are responsible for approximately 90% of cases of meningococcal meningitis. Success in the prevention of group A and C meningococcal meningitis was achieved using a bivalent polysaccharide vaccine (refs. 6 and 7). This vaccine became a commercial product and has been used successfully in the last decade in the prevention and arrest of major meningitis epidemics in many parts of the world. However, there has been a need to augment this vaccine because a significant proportion of cases of meningococcal meningitis are due to groups other than A and C. Group B is of particular epidemiologic importance, but groups Y and W135 are also significant (ref. 8). The inclusion of the group B polysaccharide in the vaccine remains a special problem. However, a tetravalent vaccine comprising groups A, C, W135, and Y is the currently used meningococcal meningitis vaccine.

The group B meningococcal polysaccharide is poorly immunogenic in man (ref. 9). Two major reasons have been proposed to account for this phenomenon. One is that the α-(2→8)-linked sialic acid homopolymer is rapidly depolymerized in human tissue because of the action of neuraminidase. The other is that Group B capsular polysaccharide (CPs) consist of poly N-acetylneuraminic acid (α 2-8 NeuNAc), α 2-8 NeuNAc is found as monomers and dimers on glycoproteins and gangliosides in adults and as polymers with at least eight repeating units in rat fetal and newborn tissues. Thus, the structure is recognized as "self" by the human immune system and in consequence, the production of antibody specific for this structure is suppressed and because of this molecular mimicry, a vaccine based on the native group B CPs could raise antibody directed against the α 2-8 NeuNAc moiety that might induce autoimmune disease.

Since the group B meningococcal capsular polysaccharide (CPs) is not immunogenic in humans, approaches have been pursued to increase its immunogenicity. One approach uses non covalent complexes of Group B CPs and outer membrane protein (OMPs) (ref. 10). Such complexes are formed by hydrophobic interaction between hydrophobic regions on the OMPs and a diacyl glycerol group present on the reducing end of the CPs (ref. 11, 12). (The chemical structures of the meningococcal Group B and C capsular polysaccharides are shown in FIG. 3). Human volunteers were given two doses of the complex at 0 and 5 weeks. The antibody response to the this complex was initially encouraging, since most individuals responded with an increase in antibodies to Group B CPs (refs. 12, 13). However, the second dose resulted in little or no increase in antibody titres which declined over a period of 14 weeks. The antibodies with specificity for the Group B polysaccharide were limited to antibodies of the IgM class (ref. 10, 12) and were directed against determinants associated only with high molecular weight polysaccharides.

In a further attempt to improve the immunogenicity of Group B CPs, Jennings et al (ref. 14) prepared a Group B meningococcal-TT conjugate (GBMP-TT) by covalently linking the CPs to tetanus toxoid (TT) through its terminal non-reducing sialic acid using periodate oxidized CPs. This procedure, however, did not result in any significant enhancement in immunogenicity (ref. 14). The antibody response elicited in animals was directed primarily against the linkage point between the CPs and the protein (GBMP-TT).

A further approach to improve the immunogenicity of the Group B CPs involved the chemical modification of the polysaccharide. Jennings et al. (ref. 15) reported that N-acetyl group of Group B CPs could be selectively removed by the action of a strong base at elevated temperature. The acetyl groups were then replaced with N-propionyl groups by propionic anhydride treatment to produce poly N-propionylneuraminic acid (a (2-8) NeuPro). The N-propionylated CPs were first periodate oxidized with sodium periodate, and then coupled to TT in the presence of sodium cyanoborohydride to provide chemically modified GBMP-TT conjugate. When mice were immunized with this conjugate formulated in Freund's complete adjuvant (FCA), high levels of IgG antibody cross-reactive with the native Group B CPs were observed. The mouse anti-serum was found to be bactericidal for all Group B strains. However, further studies revealed that two populations of antibody with different specificity were found in the sera. One population reacted with purified Group B CPs and one did not. The antibodies that did not react with the isolated Group B CPs appeared to be responsible for bactericidal activity. These antibodies may be reacting with an epitope on the cell-associated CPs that was not present on the purified CP (ref. 16).

*Neisseria meningitidis* Group B is a serious pathogen for which no vaccine exists. It would be desirable to provide alternative conjugates comprising the capsular polysaccharide of N. meningitidis conjugated to a carrier as immunogenic compositions, including vaccines, and use as and for the generation of diagnostic reagents. In particular, the capsular polysaccharides of N. meningitidis contain multiple sialic derivatives that can be modified and used to attach carrier molecules thereto.

SUMMARY OF THE INVENTION

The present invention is concerned with certain new chemical compounds which are derivatives of a Group B polysaccharide of Neisseria meningitidis and other capsular polysaccharides containing multiple sialic acid derivatives, their preparation and use in raising antibodies for diagnostic applications. The polysaccharides are modified to include linking molecules between the termini of the polysaccharide to permit the modified molecule to be joined to a carrier molecule, such as a carrier protein, for example, tetanus toxoid.

In one aspect of the present invention, there is provided a modified capsular polysaccharide containing multiple sialic acid derivatives, preferably a polysaccharide of Neisseria, more preferably the Group B polysaccharide of Neisseria meningitidis, which contains at least one moiety of the formula (I):

[Structure of formula (I) showing a sugar ring with OH, COOH, HO, HN, and A substituents]

in which A is a residue of a heterobifunctional linker molecule. The modified polysaccharide may contain up to about 5 of the moieties of formula I.

The heterobifunctional linker molecule is linked from one end to the secondary amino group through a covalent linkage and has a free end having a functional group through which the polysaccharide may be bonded to a carrier molecule.

Representative heterobifunctional linker molecules include sulfosuccinimidyl (4-iodoacetyl) aminobenzoate (Sulfo-SIAB), m-maleimidobenzoyl-N-hydroxysulfosuccinimide ester (Sulfo-MBS), N-succinimidyl 3-(2-pyridyldithio) propionate (SPOP) and sulfosuccinimidyl 4-(p-maleimidophenyl) butyrate.

The modified polysaccharide of the invention preferably also contains at least one moiety of formula (II):

[Structure of formula (II) showing a sugar ring with OH, COOH, HO, HN, and $R_1$ substituents]

wherein $R_1$ is a lower alkonyl group, preferably a propionyl or an acetyl group. The modified polysaccharides preferably consists wholly of a plurality of moieties of formula (II) and at least one moiety of formula (I), preferably up to about 5 moieties of formula (I). The modified polysaccharide preferably contains from about 10 to about 40 total number of moieties of formula (I) and formula (II).

The modified polysaccharide of the present invention, therefore, contains at least one or a plurality of pendant molecules, which enable the modified polysaccharide to be linked to a carrier molecule which may comprise a protein, a peptide or a solid matrix.

The carrier molecule may be tetanus toxoid, diphtheria toxoid, cholera toxin or an outer membrane protein of Haemophilus, including P1, P2, P6, D15 (ref. 20), Hin 47 (ref. 21), transferrin receptor, lactoferrin receptor (ref. 22) and hemin binding proteins. Depending on the number of reactive sites on the carrier, a cross-linked structure may be formed, as illustrated schematically in FIG. 2. The resulting conjugate molecule constitutes another aspect of the invention.

The modified polysaccharide may be prepared by a procedure which constitutes a further aspect of the invention. Accordingly, in this further aspect of the invention, there is provided a method of producing a modified capsular polysaccharide containing multiple sialic acid derivatives, preferably a polysaccharide of Neisseria, particularly the Group B polysaccharide of Neisseria meningitidis, which comprises:

deacetylating at least a substantial proportion and preferably substantially all of the acetyl groups from the capsular polysaccharide containing multiple sialic acid derivatives to provide a deacetylated molecule, and reacting the deacetylated molecule with (i) a heterobifunctional linker molecule having one functional group capable of reacting with free amino groups in the deacetylated molecule, in an amount sufficient to reactively couple at least one of said linker molecules to the deacetylated molecule at at least one free amino groups therein, and (ii) an alkyl acid anhydride capable of reacting with free amino groups in the deacetylated molecule, in an amount sufficient to react said alkyl acid anhydride with any free amino groups in said deacetylated molecule not reacted with said linker molecule, thereby to produce a modified capsular polysaccharide containing at least one moiety of the formula I:

[Structure of formula (I)]

and the remaining moieties of formula II:

[Structure of formula (II)]

The resulting modified polysaccharide may be reacted further with a carrier molecule to conjugate the modified polysaccharide to the carrier molecule. Such conjugation may be achieved by interaction of free functional groups on the heterobifunctional linker molecule and co-reactive groups on the carrier molecule. For example, thiol groups on a carrier protein may react with hydroxyl or thiol functional groups on the heterobifunctional linker molecule to form thiol ether and disulfide couplings respectively. Such coupling reaction may be effected without using acidic conditions which may result in loss of antigenicity of the polysaccharide.

The present invention also includes immunogenic compositions comprising the conjugate molecule provided herein which may be administered to a host in an immunoeffective amount to generate an immune response.

The conjugate molecules provided herein are useful in diagnostic procedures. Accordingly, in a further aspect of the invention, there is provided a method of determining the presence of antibodies specifically reactive with a Group B polysaccharide of a *Neisseria meningitidis* strain in a sample, comprising the steps of:

(a) contacting the sample with the conjugate molecule provided herein to produce complexes comprising the conjugate molecule and any such antibodies present in the sample specifically reactive therewith; and (b) determining the production of the complexes.

In an additional aspect of the present invention, there is provided a method of determining the presence of a Group B polysaccharide of a *Neisseria meningitidis* strain in a sample, comprising the steps of:

(a) immunizing a subject with the immunogenic composition of provided herein to produce antibodies specific for said polysaccharide;

(b) isolating the polysaccharide specific antibodies;

(c) contacting the sample with the isolated antibodies to produce complexes comprising any Group B polysaccharide of a *Neisseria meningitidis* strain present in the sample and the isolated polysaccharide specific antibodies; and (d) determining production of the complexes.

A further aspect of the present invention provides a diagnostic kit for determining the presence of antibodies in a sample specifically reactive with a Group B polysaccharide of a *Neisseria meningitidis* strain, comprising:

(a) the conjugate molecule provided herein;

(b) means for contacting the conjugate molecule with the sample to produce complexes comprising the conjugate molecule and any antibodies present in the sample; and (c) means for determining production of the complexes.

In addition, the present invention provides a diagnostic kit for determining the presence of a Group B polysaccharide of a *Neisseria meningitidis* strain in a sample, comprising:

(a) a Group B polysaccharide specific antibody to the immunogenic composition provided herein;

(b) means for contacting the antibody with the sample to produce a complex comprising the Group B polysaccharide and the antibody; and (c) means for determining the production of the complex.

The present invention further comprises a diagnostic kit for determining the presence of a Group B polysaccharide of a *Neisseria meningitidis* strain in a sample, comprising a Group B polysaccharide specific antibody to the immunogenic composition of claim 33; means for contacting the antibody with the sample to produce a complex comprising said Group B polysaccharide and the antibody; and means for determining the production of the complex.

BRIEF DESCRIPTION OF THE FIGURES

The invention will be further understood from the following description and specific Examples with reference to the Figures in which.

GENERAL DESCRIPTION OF INVENTION

As discussed above, the present invention is concerned with certain novel chemical compounds which are polysaccharides modified to contain bifunctional linker molecules between termini to enable the polysaccharides to be conjugated to carrier molecules to permit the use of the conjugates as immunogens.

Figure 3:
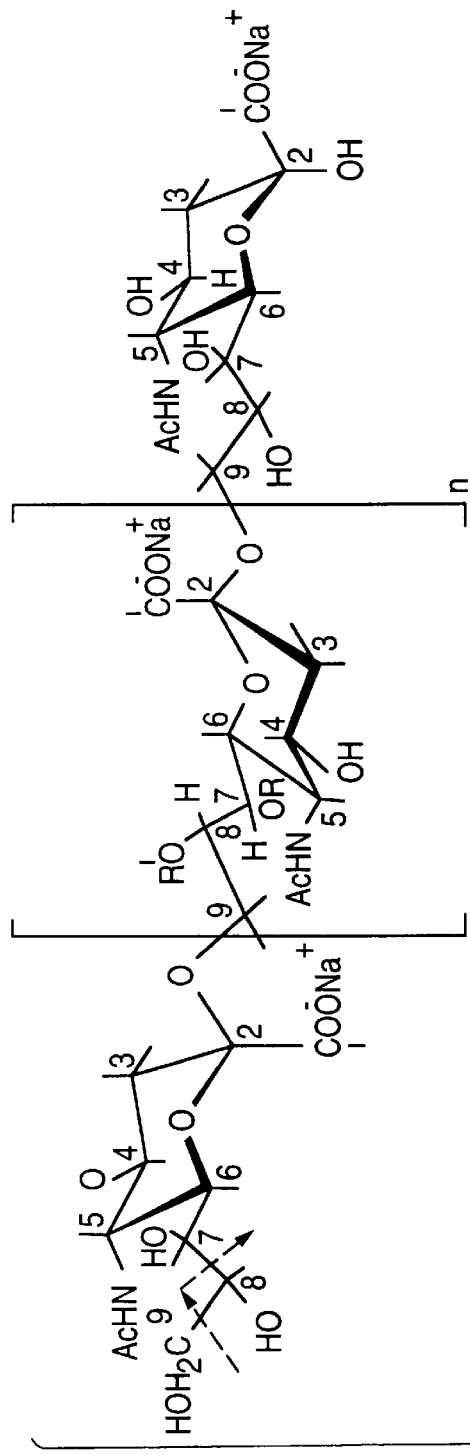
FIG. 3 shows the chemical structure of the meningococcal Group C (upper) and Group B (lower) capsular polysaccharide.
Figure 3:
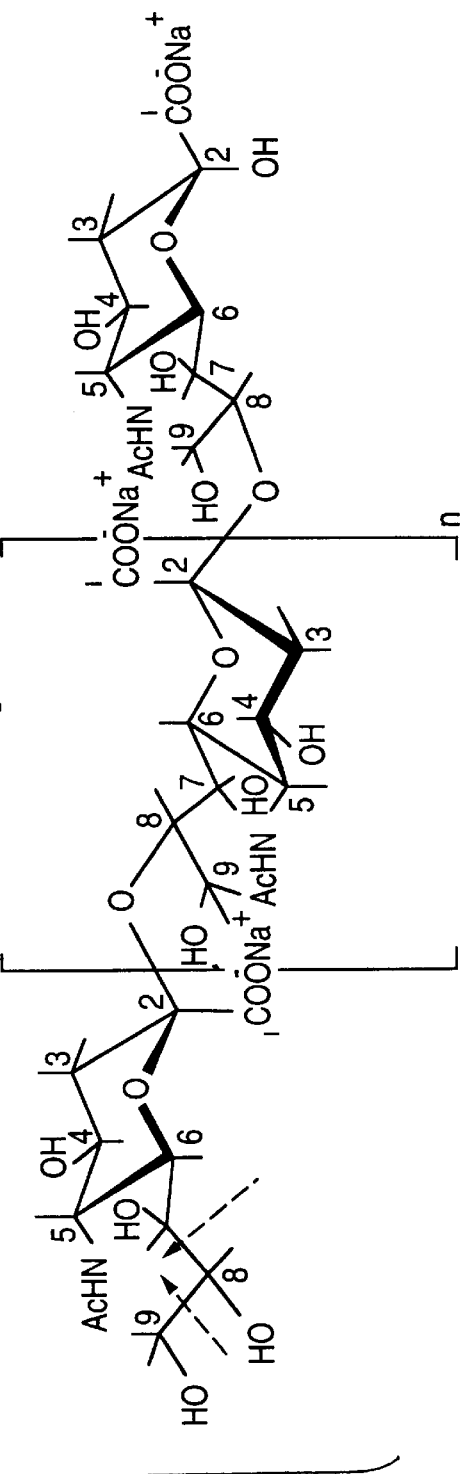

The linker molecules are introduced by first deacetylating capsular polysaccharides which contain multiple sialic acid derivatives. Such capsular polysaccharides include the Group C, Group B and Group W 135 polysaccharides of *Neisseria meningitidis*. The structures for the Group C and Group B polysaccharides are shown in FIG. 3 (see also ref. 23). Other structures are described in ref. 24. The present invention is particularly concerned with modifying the Group B polysaccharide of *Neisseria meningitidis*.

Such deacetylation may be effected by the method of Jennings et al (ref. 15). In such procedure, the polysaccharide may be dissolved in degassed aqueous sodium hydroxide solution and the solution heated to effect deacetylation. Generally, substantially complete deacetylation of the polysaccharide may be effected, for example, by heating for about 6 to 8 hours at about 100° C. to 130° C.

The deacetylated polysaccharide then is reacted with the heterobifunctional linker molecule having a group which will selectively react at one end to free amino groups on the deacetylated polysaccharide. The amount of heterobifunctional linker molecule employed is at least sufficient to introduce at least one linker molecule to the polysaccharide backbone between the termini of the polysaccharide. The resulting moiety of the polysaccharide has the formula I:

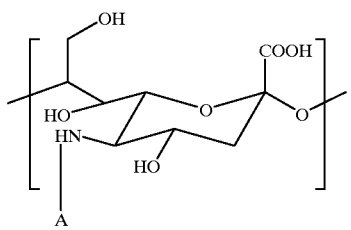

wherein A is a residue the heterofunctional linker molecule. From about 1 to about 5 such moieties may be introduced to the polysaccharide.

The free amino groups which are not reacted with the heterobifunctional linker molecule are blocked by reacting such groups with carboxylic acid groups. Such carboxylic acid groups may be provided from a sufficient quantity of an alkyl acid anhydride, preferably propionic anhydride or acetyl anhydride. The resulting moiety of the polysaccharide has the formula (II):

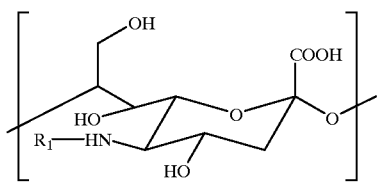

wherein $R_1$ is a lower alkonyl group.

Such reactions with the free amino groups of the deacylated polysaccharide may be effected in any convenient manner. For example, the deacylated polysaccharide may be dissolved in mildly alkaline medium, such as an aqueous sodium bicarbonate solution, and then reacted with approximately 5 to 25 molar equivalents of the bifunctional linker, such as sulfosuccinimidlyl-(4-iodoacetyl) aminobenzoate, followed by stirring in the dark for about 1 hour. The acid anhydride, for example, propionic anhydride, then may be added to the reaction mixture and stirring continued for another about 10 to 18 hours at room temperature.

The resulting polysaccharide preferably has a total of about 10 to about 40 moieties of formula I and formula II and generally consists substantially entirely of such moieties.

The provision of the bifunctional linker molecules pendant from the polysaccharide chain enables the polysaccharide molecule to be linked to a carrier molecule through the interaction of the functional group at the free end of the heterobifunctional linker molecule with reactive groups naturally present in the carrier molecule or introduced thereto by chemical modification. In one preferred embodiment, the carrier molecule is a protein having free thiol groups. The resulting conjugates exhibit an enhanced immunogenicity of the polysaccharide.

The modified polysaccharide molecule may be attached to a protein by known techniques for covalently attaching polysaccharides to proteins or polypeptides. The preferred techniques are thioester or disulfide coupling, for example, the coupling of one of the following combinations:
N-Pr-GBMP-N-4-iodoacetylbenzoate+HS-protein (a)
N-Pr-GBMP-N-m-maleimidobenzoyl+HS-protein (b)
N-Pr-GBMP-N-3-(2-pyridylthio)propionate+HS-protein (c)

Figure 1A:
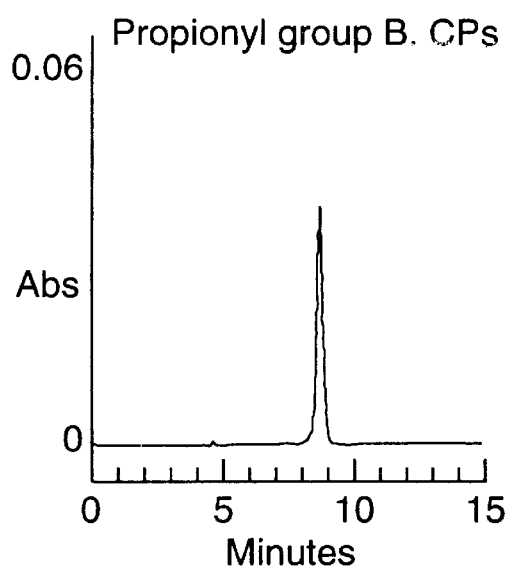
FIG. 1A shows the capillary electrophoresis chromatogram of Propionyl group B capsular polysaccharides.
Figure 1C:
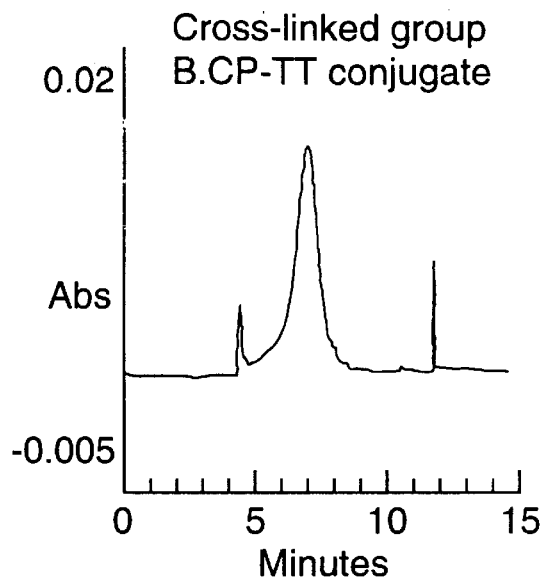
FIG. 1C shows the capillary electrophoresis chromatogram of the N-propyl-N-IAB-GBMP-TT conjugate.
Figure 1B:
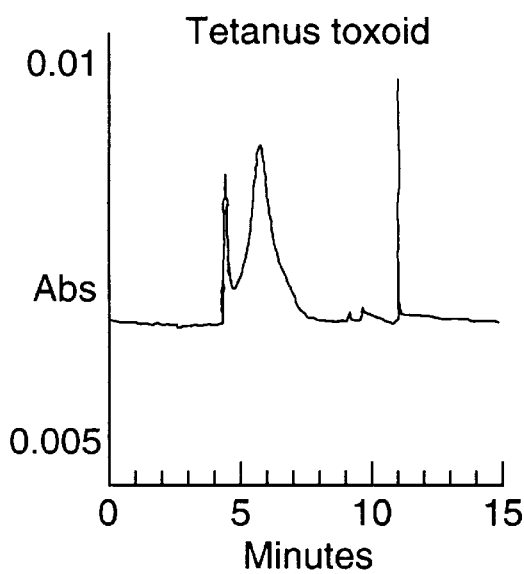
FIG. 1B shows the capillary electrophoresis chromatogram of Tetanus toxoid
Figure 1D:
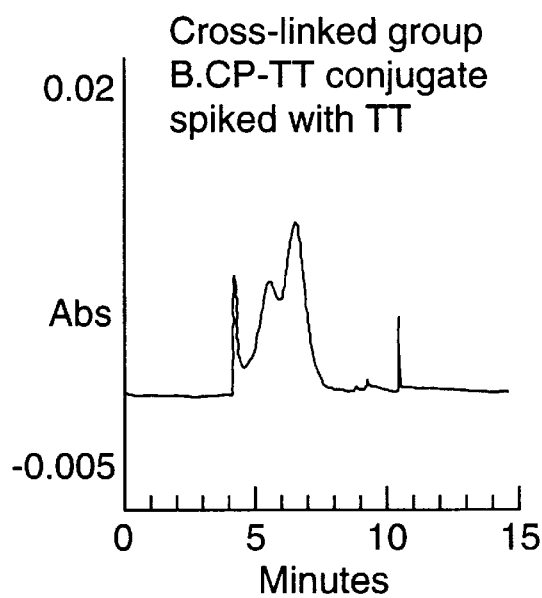
FIG. 1D shows the capillary electrophoresis chromatogram of the N-propyl-N-IAB-GBMP-TT conjugate preparation spiked with tetanus toxoid.
Figure 2:
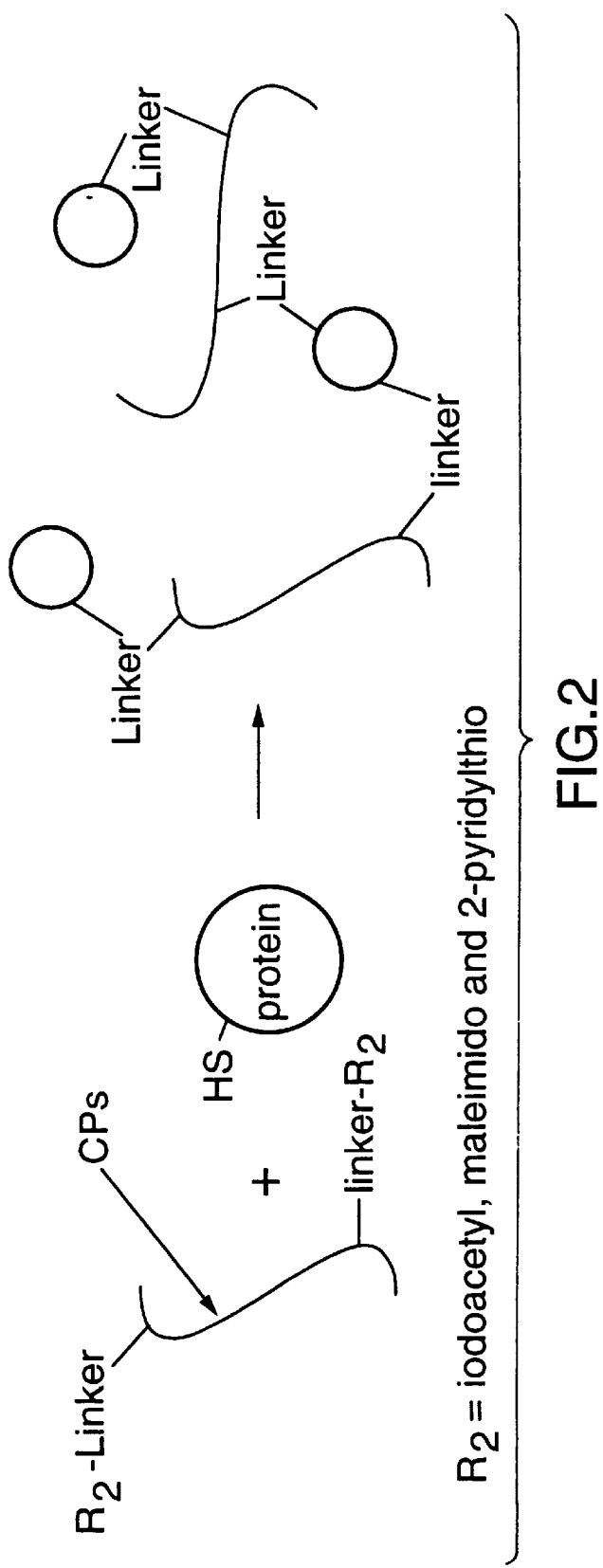
FIG. 2 shows a schematic diagram of the cross linking of protein molecules with capsular polysaccharides having pendant heterobifunctional linkers.

The reaction which takes place between the bifunctional linkers and the protein is shown substantially in FIG. 2 and, as may be seen therein, may involve cross-linking between polysaccharide chains as multiple thiol groups on the protein react with the linker molecules.

Such reaction may be effected by adding the protein, for example, tetanus toxoid, in a suitable buffer, to the modified polysaccharide in a desired molar ratio, depending upon the number of moieties of formula (I) present in the polysaccharide, for example, a molar ratio of polysaccharide to protein of from about 10 to about 100. The procedure may be effected by permitting the mixture to stand overnight at room temperature.

Any unreacted functional groups on the heterobifunctional linker molecules preferably are blocked by a suitable reagent, such as by reacting with 2-mercaptoethanol. The resulting cross-linked material then may be purified by conventional techniques. The identity of the conjugate may be determined by any convenient technique, for example, Beckman capillary electrophoresis.

The polysaccharide carrier molecule conjugates, specifically conjugate Group B polysaccharide from *N. meningitidis* and tetanus toxoid provided herein, raised antibodies to the polysaccharide in rabbits, thereby demonstrating the immunogenic nature of the molecules and their utility as immunogenic preparation and as diagnostic reagents and for the production of diagnostic reagents.

Vaccine preparation and use

As indicated above, the present invention, in one embodiment, provides conjugates useful for formulating immunogenic compositions, suitable to be used as, for example, vaccines. The immunogenic composition elicits an immune response by the host to which it is administered including the production of antibodies by the host.

The immunogenic compositions may be prepared as injectables, as liquid solutions or emulsions. The antigens and immunogenic compositions may be mixed with physiologically acceptable carriers which are compatible therewith. These may include water, saline, dextrose, glycerol, ethanol and combinations thereof. The vaccine may further contain auxiliary substances, such as wetting or emulsifying agents or pH buffering agents, to further enhance their effectiveness. Vaccines may be administered by injection subcutaneously or intramuscularly.

Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories may be desirable. For suppositories, binders and carriers may include, for example, polyalkylene glycols and triglycerides. Oral formulations may include normally employed incipients, such as pharmaceutical grades of saccharine, cellulose and magnesium carbonate.

These compositions may take the form of solutions, suspensions, tablets, pills, capsules, sustained release formulations or powders and contain 1 to 95% of the immunogenic compositions of the present invention.

The immunogenic compositions are administered in a manner compatible with the dosage formulation, and in such amount as to be therapeutically effective, protective and immunogenic. The quantity to be administered depends on the subject to the immunized, including, for example, the capacity of the subject's immune system to synthesize antibodies, and if needed, to produce a cell-mediated immune response. Precise amounts of antigen and immunogenic composition to be administered depend on the judgement of the practitioner. However, suitable dosage ranges are readily determinable by those skilled in the art and may be of the order of micrograms to milligrams. Suitable regimes for initial administration and booster doses are also variable, but may include an initial administration followed by subsequent administrations. The dosage of the vaccine may also depend on the route of administration and will vary according to the size of the host.

The concentration of antigen in an immunogenic composition according to the invention is in general 1 to 95%. A vaccine which contains antigenic material of only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens.

Immunogenicity can be significantly improved if the antigens are co-administered with adjuvants, commonly used as 0.005 to 0.5 percent solution in phosphate buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune response.

Immunostimulatory agents or adjuvants have been used for many years to improve the host immune responses to, for example, vaccines. Intrinsic adjuvants, such as lipopolysaccharides, normally are the components be the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and, more recently, a HBsAg vaccine has been adjuvanted with alum. While the usefulness of alum is well established for some applications, it has limitations. For example, alum is ineffective for influenza vaccination and inconsistently elicits a cell mediated immune response. The antibodies elicited by alum-adjuvanted antigens are mainly of the IgG1 isotype in the mouse, which may not be optimal for protection by some vaccinal agents.

A wide range of extrinsic adjuvants can provoke potent immune responses to antigens. These include saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are often emulsified in adjuvants. Many adjuvants are toxic, inducing granulomas, acute and chronic inflammations (Freund's complete adjuvant, FCA), cytolysis (saponins and Pluronic polymers) and pyrogenicity, arthritis and anterior uveitis (LPS and MDP). Although FCA is an excellent adjuvant and widely used in research, it is not licensed for use in human or veterinary vaccines because of its toxicity.

Desirable characteristics of ideal adjuvants include:
(1) lack of toxicity;
(2) ability to stimulate a long-lasting immune response;
(3) simplicity of manufacture and stability in long-term storage;
(4) ability to elicit both CMI and HIR to antigens administered by various routes;
(5) synergy with other adjuvants;
(6) capability of selectively interacting with populations of antigen presenting cells (APC);
(7) ability to specifically elicit appropriate T.1 or TH2 cell-specific immune responses; and
(8) ability to selectively increase appropriate antibody isotype levels (for example, IgA) against antigens.

U.S. Pat. No. 4,855,283 granted to Lockhoff et al on Aug. 8, 1989 which is incorporated herein by reference thereto teaches glycolipid analogues including N-glycosylamides, N-glycosylureas and N glycosylcarbamates, each of which is substituted in the sugar residue by an amino acid, as immune-modulators or adjuvants. Thus, Lockhoff et al. (U.S. Pat. No. 4,855,283 and ref. 18) reported that N-glycolipid analogs displaying structural similarities to the naturally-occurring glycolipids, such as glycosphingolipids and glycoglycerolipids, are capable of eliciting strong immune responses in both herpes simplex virus vaccine and pseudorabies virus vaccine. Some glycolipids have been synthesized from long chain alkylamines and fatty acids that are linked directly with the sugars through the anomeric carbon atom, to mimic the functions of the naturally occurring lipid residues.

U.S. Pat. No. 4,258,029 granted to Moloney, assigned to the assignee hereof and incorporated herein by reference thereto, teaches that octadecyl tyrosine hydrochloride (OTH) functions as an adjuvant when complexed with tetanus toxoid and formalin inactivated type I, II and III poliomyelitis virus vaccine. Also, Nixon-George et al. (ref. 19), reported that octodecyl esters of aromatic amino acids complexed with a recombinant hepatitis B surface antigen, enhanced the host immune responses against hepatitis B virus.

Immunoassays

In one embodiment, the conjugates of the present invention are useful for the production of immunogenic compositions that, can be used to generate antigen-specific antibodies that are useful in the specific identification of that antigen in an immunoassay according to a diagnostic embodiment. Such immunoassays include enzyme-linked immunosorbent assays (ELISA), RIAs and other non-enzyme linked antibody binding assays or procedures known in the art. In ELISA assays, the antigen-specific antibodies are immobilized onto a selected surface; for example, the wells of a polystyrene microtiter plate. After washing to remove incompletely adsorbed antibodies, a nonspecific protein, such as a solution of bovine serum albumin (BSA) or casein, that is known to be antigenically neutral with regard to the test sample may be bound to the selected surface. This allows for blocking of nonspecific adsorption sites on the immobilizing surface and thus reduces the background caused by nonspecific bindings of antigens onto the surface. The immobilizing surface is then contacted with a sample, such as-clinical or biological materials, to be tested in a manner conducive to immune complex (antigen/antibody) formation. This may include diluting the sample with diluents, such as BSA, bovine gamma globulin (BGG) and/or phosphate buffered saline (PBS)/Tween. The sample is then allowed to incubate for from about 2 to 4 hours, at temperatures such as of the order of about 25° to 37° C. Following incubation, the sample-contacted surface is washed to remove non-immunocomplexed material. The washing procedure may include washing with a solution, such as PBS/Tween or a borate buffer.

Following formation of specific immunocomplexes between the antigen in the test sample and the bound antigen-specific antibodies, and subsequent washing, the occurrence, and even amount, of immunocomplex formation may be determined by subjecting the immunocomplex to a second antibody having specificity for the antigen. To provide detecting means, the second antibody may have an associated activity, such as an enzymatic activity, that will generate, for example, a colour development upon incubating with an appropriate chromogenic substrate. Quantification may then achieved by measuring the degree of colour generation using, for example, a visible spectra spectrophotometer. In an additional embodiment, the present invention includes a diagnostic kit comprising antigen-specific antibodies generated by immunization of a host with immunogenic compositions produced according to the present invention.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Example 1

This Example describes the preparation and characterization of modified *Neisseria meningitidis* group B capsular polysaccharide.

*N. meningtidis* group B capsular polysaccharide was purchased from Sigma. The polysaccharide was de-acetylated essentially according to the method of Jennings et al (ref. 15) at a temperature of about 110° to 120° C. The polysaccharide was dissolved in degassed sodium hydroxide (2M) and the resulting mixture was then heated for 6 to 8 hours at about 100° to 130° C.

The product was isolated by a combination of pH neutralization (hydrochloric acid, 2M), dialysis (four changes of 10 mM ammonium bicarbonate, 4° C.) and lyophilization. This procedure resulted in 100% de-acetylation, as determined from the complete disappearance of the acetyl signal in the $^1$H NMR spectrum.

The N-deacetylated GBMP (21.5 mg) was dissolved in sodium bicarbonate (25 mM, 3.00 mL) and Sulfo-SIAB (5–50 equivalents) were added over 15 minutes. The mixture was then stirred for one hour at room temperature in the dark. Sodium bicarbonate (18 mg) was added to the mixture, followed by the addition of three aliquots (125 μL each) of propionic anhydride over a 15 minute period. After stirring the mixture overnight in the dark, the mixture was dialyzed exhaustively against water at 4° C. and then freeze-dried to yield N-propyl-N-{ (4-iodoacetyl) aminobenzoate} GBMP (25.4 mg). The colominic acid content was determined using the resorcinol method (ref. 16), whereas the iodide content of the derivatized polysaccharides was determined using modified Ellman's test (ref. 17) and was found to be 1 to 5 mole of iodine per mole of polysaccharides.

Example 2

This Example describes the preparation and characterization of the N-Propionylated-N-IAB-GBMP-TT conjugate.

To synthesize the protein-polysaccharide conjugate, the modified N-propyl-N-linker GBMP prepared as described in Example 1 above, was dissolved in phosphate buffer, pH 8.0, at a 2–10 mg/mL. Tetanus toxoid was added to a final molar ratio of 10–100 to 1 of polysaccharide to protein. The total mixture was then stirred at room temperature in the dark for 24 hours. Two microliters of 2-mercaptoethanol were added and the mixture was stirred for an additional 18 hours. The mixture was then exhaustively dialyzed against water (4×4 L) in a cold room at 4° C. using molecularporous membrane (3500 mol. wt. cutoff). The product was concentrated to 3.0 mL using an Amicon 100 ultrafiltration unit then repeatedly concentrated using PBS buffer as a diluent. Purity of the final product was determined using a Beckman capillary electrophoresis model 2050 (CE), using a fused silica capillary tube (75 μm i.d., 50 cm) and borate buffer (100 mM, pH 8.3) as mobile phase. UV detection at 200 nm allowed detection of the conjugate (7.3 min), free group B CPs (9.3 min) and TT (5.8 min) at an applied potential of 15 KV. Using a 10 sec injection time and a concentration of 470 to 500 μg/mL of either protein or carbohydrate, the chromatograms shown in FIG. 1 were obtained. FIGS. 1*a*, 1*b*, 1*c* and 1*d* represent the unconjugated free propionylate GBMP, TT, N-propyl-N-IAB-GBMP-TT, and the N-propyl-N-IAB-GBMP-TT conjugate spiked with TT respectively. Samples were analyzed in 100 mm phosphate buffer. To determine the molar ratio of protein to polysaccharide in the conjugate 150 μL of water, 25 μL of 100% trichloroacetic acid were added to 350 μL of the conjugate mixture and this mixture placed in an ice bath at 5° C. for 30 minutes. The pellets were centrifuged, redissolved in water (500 μL) and additional trichloroacetic acid (25 μL) was added. The mixture was cooled again, centrifuged and the resulting pellets were reconstituted in a final volume of 1 mL of water. This mixture was then assayed for protein using Bio-Rad assay and colominic acid using resorcinol assay. The data are shown in Table 1 below.

Example 3

This Example describes the preparation of native GBMP-TT conjugate.

To 26 mg of periodate oxidized native Group B meningococcal CP (prepared by treating native polysaccharides with sodium metaperiodate as described by Jennings et al) (ref. 25) in 1.0 M phosphate buffer, pH 8.5, was added tetanus toxoid (3.3 mg) and sodium cyanoborohydride (20 mg). The solution was stirred for 7 days at 38° C., after which the mixture was dialyzed against PBS buffer (4×4 L) at 3–8° C. and concentrated using an Amicon 10 ultrafiltration unit. The composition of the conjugate was assayed for protein using a Bio-Rad assay and colominic acid using resorcinol assay and the results are shown in Table 1 below.

Example 4

This Example describes the preparation of N-propionyl GBMP-TT conjugate.

N-deacetylated GBMP (67 mg) was dissolved in saturated sodium bicarbonate (10 mL) and three aliquots of propionic anhydride (0.250 mL) were added over a 15 minute period. The total mixture was then stirred at room temperature overnight. Ninhydrine test was negative indicating complete conversion of free amino groups to propionamido groups. The mixture was then dialyzed against distilled water and lyophilized to afford the propionylated GBMP (50 mg). 'H NMR spectra revealed the presence of $CH_3$ and $CH_2$ signals.

The polysaccharide protein conjugate was prepared from 41 mg of periodate oxidized N-propionylated GBMP (prepared by treating the propiolated polysaccharides with sodium metaperiodate as described by Jennings et al) (ref. 18) and 3.3 mg of tetanus toxoid as described above. The composition of the GBMP-protein conjugates were assayed for protein using Bio-Rad assay and colominic acid using resorcinol assay and the result are shown in Table 1 below.

Example 5

This Example describes the preparation of native GBMP-BSA conjugate.

50 mg of periodate oxidized native CPs were dissolved in 5 mL of phosphate buffer, pH 8.5, 5mg of BSA and 20 mg of sodium cyanoborohydride were added and the mixture was stirred for 7 days at 38° C. The mixture was then dialyzed exhaustively against PBS (4×4 L) at 4° C. This conjugate was found to contain 5% of CP to BSA as determined by both resorcinol and Bio-Rad Coomassie Blue assay. The conjugate was diluted to a final protein concentration of 1 mg/mL and was used as target antigen in ELISAS.

Example 6

This Example describes the immunization of rabbits with conjugates.

Rabbits were immunized intramuscularly (i. m.) with 500 µL of polysaccharide-protein conjugates (1–50 µg polysaccharide equivalent) prepared as described in preceding examples mixed with 3 mg AlPO4 per mL, followed by two booster doses at two week intervals. Antisera were collected every 2 weeks after the first injection, heat inactivated at 56° C. for 30 min and stored at −20° C.

To measure anti-capsular polysaccharide antibodies, microtiter plate wells (Nunc-Immunoplate, Nunc, Denmark) were coated with 200 ng of purified group B CP-BSA in 200 µL of coating buffer (15 mM $Na_2CO_3$, 35 mM $NaHCO_3$, pH 9.6) for 16 hours at room temperature. The plates were then blocked with 0.1% (W/V) BSA in phosphate buffer saline PBS for 30 min at room temperature. Serially diluted antisera raised against group B CP conjugates were added to the wells and incubated for 1 hour at room temperature. After removal of antisera, the plates were washed five times with PBS containing 0.1% (w/v) Tween-20 and 0.1% (w/v) BSA. F(ab')$_2$ from goat anti-rabbit IgG antibodies conjugated to horseradish peroxidase (Jackson ImmunoResearch Labs Inc., PA) were diluted (⅛,000) with washing buffer, and added onto the microtiter plates. After 1 hour incubation at room temperature, the plates were washed five times with the washing buffer. The plates were then developed using the substrate tetramethylbenzidine (TMB) in $H_2O_2$(ADI, Toronto), the reaction was stopped with 1N $H_2SO_4$ and the optical density was measured at 450 nm using a Titretek Multiskan II (Flow Labs., Virginia). A standard anti-group B CP antiserum was included as positive control. Assays were performed in triplicates and the reactive titer of an antiserum was defined as the dilution consistently showing a two-fold increase in O.D. value over that obtained with the pre-immune sera.

The results are shown in Table 2 below and show that antibodies raised by immunization with the N-propionylated-N-1AB-GBMP-TT conjugate specifically recognize both native group B meningococcal polysaccharide and propronyl group B meningococcal polysaccharide.

TABLE 1

Characterization of GBMP-Protein

| Conjugate | % Yield of CHO[1] | % Yield of protein[2] | SIAB/CHO mole | CHO/Protein ratio wt/wt | CHO/Protein ratio mole/mole[3] |
|---|---|---|---|---|---|
| Native GBMP-TT | 1.5 | 39.0 | — | 0.399 | 5.0 |
| Propionyl-GBMP-TT | 0.6 | 49.9 | — | 0.125 | 1.8 |
| N-propionyl-N-IAB-GBMP-TT conjugate | 0.22 | 59.9 | 2.1 | 0.029 | 0.57 |

[1]Carbohydrate present in the conjugate as determined from trichloroacetic acid (TCA) precipitation at 5° C. of an aliquot from the conjugate.
[2]Protein concentration as determined by Bio-Rad assay
[3]The molar ratio present in the conjugates was calculated with an estimated molecular weight of 10,000 for polysaccharides and 145,000 for TT.
GBMP - Group B meningococcal polysaccharide
TT - Tetanus Toxoid

TABLE 2

Immunogenicity of GBMP-Protein Conjugates in Rabbits[a]

| Immunogen | Dose (µg carbohydrate) | Reciprocal Antibody Titres Antisera reacted with native GBMP-BSA conjugate | Reciprocal Antibody Titres Antisera reacted with propionylated GBMP-BSA conjugate |
|---|---|---|---|
| Phosphate buffered saline (control) | — | <10 | <10 |
| Native-GBMP-TT[b] | 2.0 | 1000 | 5600 |
| Propionyl-GBMP-TT[c] | 2.0 | 250 | 34000 |
| N-Propionylated-N-IAB-GBMP-TT[d] | 1.4 | 900 | 6250 |

[a]Rabbits were injected i.m. three times, at 2 week intervals with 0.5 mL of each conjugate (1–50 µg polysaccharide equivalent) containing alum (3 mg/mL) as adjuvant. The animals were bled before each injection and two weeks after the last injection.
[b]-native group B. meningococcal polysaccharide-TT conjugate.
[c]-propionyl group B. meningococcal polysaccharide-TT conjugate
[d]-cross-linked-N-prionyl group B. meningococcal polysaccharide-TT conjugate

REFERENCES

1. Jackson, L. A., and Wenger, J. D. Laboratory-based surveillance for meningococcal disease in selected areas, United States, 1989–1991, MMW R 1993, 42: 21–30
2. Peltola, H.; Kayhty, H.; Makela, P. H. (1977) *Haemophilus influenzae* type b capsular polysaccharide vaccine in children: a double blind field study of 100,00 vaccinees 3 months to 5 years of age in Finland, *Pediatrics* 60: 730–737
3. Gotschlich E C (1984) Meningcococcal meningitis. In: Germanier E (ed) *Bacterial vaccines*, Academic, New York, pp. 237–255.
4. Ding, S. Q., Ye R. B., Zhang H. C. (1981) Three new serogroups of *Neisseria meningitidis*, *J. Biol. Stand* 9: 307–315
5. Ashton F E, Ryan A. Diena B. Jennings H J (1983) A new serogroup (L) of *Neisseria meningitidis*, *J. Clin. Microbiol.* 17: 722–727
6. Gotschlich E C, Goldschneider I, Artenst2ein M S (1969a) Human immunity to the meningococcus IV. Immunogenicity of group A and group C meningococcal polysaccharides. *J. Exp Med.* 129: 1367–1384
7. Artenstein M S, Gold R., Zimmerly J G, Wyle F A, Schneider H. Harkins C. (1970) Prevention of meningococcal disease by group C polysaccharide vaccine. *N Engl. J. Med.* 282: 417–420
8. Cadoz M, Armand J. Arminjon F., Gire R., Lafaix C. (1985) Tetravelent (Ak C, Y, W135) meningococcal vaccine in children: immunogenicity and safety, *Vaccine* 3: 340–342
9. Wyle F A, Artenstein M S, Brandt B L, Tramont E C, Kasper D L, Altieri P L, Berman S L, Lowenthal J P (1972) Immunologic response of man to group B meningococcal polysaccharide vaccines. *J. Infect Dis.* 126: 514–521
10. Zollinger, W. D. Mandrell, R. E., Griffiss, J. M., Altieri, P., and Berman, S. 1979, *J. Clin. Invest.* 63, 836.
11. Gotschlich, E. C., Fraser, B. A., Nishimura, D., Robbins, J. B. Liu, T.-Y. 1981, *J. Biol. Chem.* 256, 8915.
12. Zollinger, W. D., Mandrell, R. E., Griffiss, J. M. Seminars in Infection Disease. New York, Thieme-Stranon, 1980, vol 4: *Bacterial Vaccines*, pp 254.
13. Mandrell, R. E., Zollinger, R. E., 1982, *J. Immunol.* 129, 2172.
14. Jennings, H. J., Lugowsky, C 1981, *J. Immunol.* 127, 1011.
15. Jennings, H. J., Roy, R., Gamian, A. 1986, *J. Immunol.* 137, 1708.
16. Svennerholm, L. (1957), *Biochimica and Biophysica Acta.* 24, 604.
17. Jennings, H. J.(1989), Cruse, J. M, Lewis, R. E. Jr. (eds): *Conjugate Vaccines*. Basel, Karger, vol 10, pp 151–165.
18. Lockhoff, O. Glycolipids as Immmunomodulators: Synthesis and Properties. (1991), *Chem. Int. Ed. Engl.* 30:1611–1620.
19. Nixon-George et al. (1990), *J. Immunology* 144: 4798–4802.
20. WO 94/12641
21. WO 92/10936
22. U.S. Pat. No. 5,141,743
23. Jennings, H J., Capsular Polysaccharides as Vaccine Candidates. Current Topics in Microbiology and Immunology. 1990, 150: 97–127
24. Jennings, H J., Capsular Polysaccharides as human vaccines. Advances in Carbohydrate Chemistry and Biochemistry, 1983, 41: 155.
25. Jennings, H. J., Roy, R, Michon, F. (1985), *J. Immunol.* 134, 2651.

What we claim is:

1. A conjugate molecule, comprising:
   a modified capsular polysaccharide containing multiple sialic acid derivations which contains at least one moiety of formula (I):

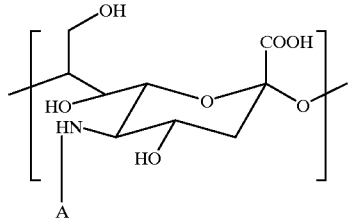

wherein A is a residue of a heterobifunctional linker molecule, and
   a carrier molecule linked to said modified polysaccharide through said bifunctional molecule.

2. The conjugate molecule of claim 1 which contains up to about 5 of the moieties of formula (I).

3. The conjugate molecule of claim 1 which also contains at least one moiety of the formula (II):

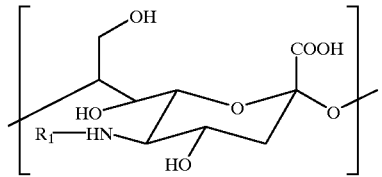

wherein $R_1$ is a lower alkonyl group.

4. The conjugate molecule of claim 1 which consists of a plurality of moieties of formula (II) and at least one moiety of formula (I).

5. The conjugate molecule of claim 4 which contains up to about 5 moieties of formula (I).

6. The conjugate molecule of claim 5 which contains from about 10 to about 40 total moieties of formula (I) and formula (II).

7. The conjugate molecule of claim 5 wherein said heterobifunctional linker molecule is selected from the group consisting of sulfosuccinimidyl(4-iodoacetyl) aminobenzoate, m-maleimidobenzoyl-N-hydroxysulfosuccinimide ester, N-succinimidyl 3-(2-pyridyldithio)propionate, and sulfosuccinimidyl 4-(p-maleimidophenyl)butyrate.

8. The conjugate molecule of claim 7 wherein said $R_1$ group is a propionyl group.

9. The conjugate molecule of claim 1 wherein said carrier molecule is a protein, a peptide or a solid matrix.

10. The conjugate molecule of claim 8 wherein said protein is selected from the group consisting of tetanus toxoid, diphtheria toxoid, cholera toxin and an outer membrane protein of Haemophilus, including P1, P2, P6, D15, Hin 47, transferrin receptor, lactoferrin receptor, and hemin binding proteins.

11. The conjugate molecule of claim 1 wherein said capsular polysaccharide is a polysaccharide of Neisseria.

12. The conjugate of claim 11 wherein said Neisseria capsular polysaccharide is a Group B polysaccharide of *Neisseria meningitidis*.

13. A method of forming a modified capsular polysaccharide containing multiple sialic acid derivatives, which comprises:
   deacetylating at least a substantial proportion of the acetyl groups from the capsular polysaccharide containing multiple sialic acid groups to provide a deacetylated molecule, and reacting said deacetylated molecule with
(i) a heterobifunctional linker molecule having one functional group capable of reacting with free amino groups in the deacetylated molecule in an amount sufficient to reactively couple at least one of said linker molecules to the deacetylated molecule at at least one free amino group contained therein, and
(ii) an alkyl acid anhydride capable of reacting with free amino groups in the deacetylated molecule, in an amount sufficient to react said alkyl acid anhydride with any free amino groups in said deacetylated molecule not reacted with said linker molecule, thereby to produce a modified capsular polysaccharide containing at least one moiety of the formula I:

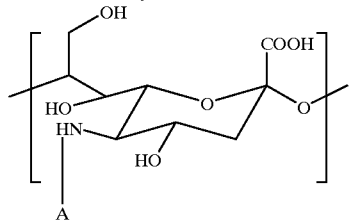

wherein A is a heterobifunctional linker molecule and the remaining moieties of formula II:

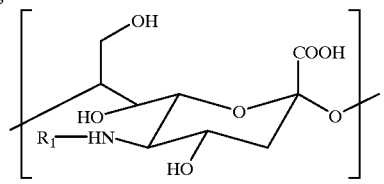

wherein $R_1$ is a lower alkanoyl group.

14. The method of claim 13 wherein substantially all the acetyl groups are removed.

15. The method of claim 13 wherein said heterobifunctional linker is employed in an amount sufficient to provide from about 1 to about 5 of the moieties of formula (I).

16. The method of claim 15 wherein said modified polysaccharide contains a total of from about 10 to about 40 moieties of formula (I) and formula (II).

17. The method of claim 16 wherein said heterobifunctional linker is selected from the group consisting of sulfosuccinimidyl(4-iodoacetyl)aminobenzoate (sulfo SIAB), m-maleimidobenzoyl-N-hydroxysulfosuccinimide ester (sulfo-MBS), N-succinimidyl 3-(2-pyridyldithio) propionate (SPDP), and sulfosuccinimidyl 4-(p-maleimidophenyl)butyrate.

18. The method of claim 17 wherein said alkyl acid anhydride is propionic anhydride or acetic anhydride.

19. The method of claim 18 including further comprising reacting the free functional group on said heterobifunctional linker molecule on said modified polysaccharide with a carrier molecule to couple the carrier molecule to the modified polysaccharide through the heterobifunctional linker molecule.

20. The method of claim 19 wherein said carrier molecule is a protein, a peptide or a solid matrix.

21. The method of claim 13 wherein said capsular polysaccharide is a polysaccharide of Neisseria.

22. The method of claim 21 wherein said Neisseria capsular polysaccharide is a Group B polysaccharide of *Neisseria meningitidis*.

23. An immunogenic composition, comprising a conjugate molecule as claimed in claim 1 and a carrier therefor.

24. A method of generating an immune response in a host, comprising administering thereto an immuno-effective amount of the immunogenic composition of claim 23.

25. A method of determining the presence of antibodies specifically reactive with a capsular polysaccharide containing multiple sialic acid groups in a sample, comprising the steps of:
(a) contacting the sample with the conjugate molecule of claim 1 to produce complexes comprising the conjugate molecule and any said antibodies present in the sample specifically reactive therewith; and
(b) determining production of the complexes.

26. The method of claim 25 wherein said capsular polysaccharide is a Group B polysaccharide of *Neisseria meningitidis*.

27. A method of determining the presence of a capsular polysaccharide containing multiple sialic acid groups in a sample, comprising the steps of:
(a) immunizing a subject with the immunogenic composition of claim 23 to produce antibodies specific for said polysaccharide;
(b) isolating the polysaccharide specific antibodies;
(c) contacting the sample with the isolated antibodies to produce complexes comprising any said capsular polysaccharide present in the sample and said isolated polysaccharide specific antibodies; and
(d) determining production of the complexes.

28. The method of claim 27 wherein said capsular polysaccharide is a Group B polysaccharide of *Neisseria meningitidis*.

29. A diagnostic kit for determining the presence of antibodies in a sample specifically reactive with Group B polysaccharide of a *Neisseria meningitidis* strain, comprising:
(a) the conjugate molecule of claim 1;
(b) means for contacting the conjugate molecule with the sample to produce complexes comprising the conjugate molecule and any said antibodies present in the sample; and
(c) means for determining production of the complexes.

30. A diagnostic kit for determining the presence of a Group B polysaccharide of a *Neisseria meningitidis* strain in a sample, comprising:
(a) a Group B polysaccharide specific antibody to the immunogenic composition of claim 23;
(b) means for contacting the antibody with the sample to produce a complex comprising said Group B polysaccharide and the antibody; and
(c) means for determining the production of the complex.

31. A method of producing monoclonal antibodies specific for a capsular polysaccharide containing multiple sialic acid group comprising:
(a) administering the conjugate molecule of claim 1 to at least one mouse to produce at least one immunized mouse;
(b) removing B-lymphocytes from the at least one immunized mouse;
(c) fusing the B-lymphocytes from the at least one immunized mouse with myeloma cells, thereby producing hybridomas;
(c) cloning the hybridomas;
(d) selecting clones which produce anti-polysaccharide antibodies;
(e) culturing the anti-polysaccharide antibody-producing clones; and then
(f) isolating anti-polysaccharide antibodies from the cultures.

* * * * *